United States Patent [19]

Nakazawa et al.

[11] 4,334,020
[45] Jun. 8, 1982

[54] METHOD OF PRODUCING L-GLUTAMIC ACID BY FERMENTATION

[75] Inventors: Hidetsugu Nakazawa, Kawasaki; Ichiro Yamane, Yamato; Eiichi Akutsu, Yokohama, all of Japan

[73] Assignee: Ajinomoto Company Incorporated, Tokyo, Japan

[21] Appl. No.: 157,012

[22] Filed: Jun. 6, 1980

[30] Foreign Application Priority Data

Jun. 20, 1979 [JP] Japan ................................. 54/78294

[51] Int. Cl.³ .............................................. C12P 13/14
[52] U.S. Cl. ................................... 435/110; 435/843; 435/840; 435/111; 435/172
[58] Field of Search ........................ 435/110, 172, 111

[56] References Cited

FOREIGN PATENT DOCUMENTS 52-2038088 3/1977 Japan .................................. 435/110

OTHER PUBLICATIONS

Tosaka et al. in Chemical Abstracts, vol. 91: 156040c, (1979) Abstr. of Japan Kokai 79 89,085, Jul. 14, 1979.

Primary Examiner—Lionel M. Shapiro
Attorney, Agent, or Firm—Oblon, Fisher, Spivak, McClelland & Maier

[57] ABSTRACT

A mutant of the genus Brevibacterium or Corynebacterium resistant to a compound having vitamine-P activity produces L-glutamic acid in a high yield, when it is cultured in an aqueous medium aerobically.

3 Claims, No Drawings

METHOD OF PRODUCING L-GLUTAMIC ACID BY FERMENTATION

BACKGROUND OF THE INVENTION

This invention relates to a method of producing L-glutamic acid by fermentation.

In order to obtain the best yield of L-glutamic acid in known fermentation proceses, the amount of L-biotin in the fermentation medium should be controlled in a very narrow range. However, beet or cane molasses, which are available as the carbon sources in a reasonable price, contain very high amount of biotin, and then the fermentation medium composed with such molasses inevitably contain excessive amount of biotin. In order to avoid the undesirable affection of excessive amount of biotin on L-glutamic acid production, surfactants, or antibiotics are added to the fermentation medium when excessive amount of biotin is contained in the known method.

SUMMARY OF THE INVENTION

It is now found that mutants of the genus Brevibacterium or Corynebacterium which are resistant to a compound having vitamine-P activity (hereinafter referred to as "vitamine-P compound") produce L-glutamic acid in a remarkably high yield, even when they are cultured without addition of surfactants or antibiotics in the fermentation medium containing the excessive amount of biotin.

Now, it is provided a method for producing L-glutamic acid which comprises culturing in an aqueous culture medium a mutant of the genus Brevibacterium or Corynebacterium which is resistant to a vitamine-P compound and recovering L-glutamic acid accumulated in the resulted culture liquid.

DESCRIPTION OF THE PREFERRED EMBODIMENTS

Specimens of the mutants used in the process of this invention are:
Brevibacterium flavum AJ 11355
  (FERM-P 5007, NRRL B-12128)
  (Esculetin)
Brevibacterium flavum AJ 11356
  (FERM-P 5008, NRRL B-12129)
  (Coumarin)
Brevibacterium flavum AJ 11357
  (FERM-P 5009, NRRL B-12130)
  (Dicumarol)
Brevibacterium lactofermentum AJ 11360
  (FERM-P 5012, NRRL B-12133)
  (Esculetin)
Brevibacterium lactofermentum AJ 11361
  (FERM-P 5013, NRRL B-12134)
  (Coumarin)
Brevibacterium lactofermentum AJ 11362
  (FERM-P 5014 NRRL B-12135)
  (Dicumarol)
Corynebacterium glutamicum AJ 11365
  (FERM-P 5017, NRRL B-12138)
  (Esculetin)
Corynebacterium glutamicum AJ 11366
  (FERM-P 5018, NRRL B-12139)
  (Coumarin)
Corynebacterium glutamicum AJ 11367
  (FERM-P 5019 NRRL B-12140)
  (Dicumarol)

The mutants of Brevibacterium flavum, Brevibacterium lactofermentum and Corynebacterium glutamicum were derived from the parent strains, Brevibacterium flavum ATCC 14067, Brevibacterium lactofermentum ATCC 13869 and Corynebacterium glutamicum ATCC 13032, respectively. Brevibacterium divaricatum ATCC 14020, Brevibacterium saccharoliticum ATCC 14066, Corynebacterium acetoacidophilum ATCC 13870, and other glutamic acid-producing bacteria of the genera Corynebacterium and Brevibacterium can be used as the parent strains.

The parent strains can be mutated to obtain the mutants of this invention by a conventional manner such as UV-rays-radiation, X-ray-radiation, exposure to a mutagen. For instance, the parent strain is mutated by exposing to 250 μg/ml N-nitro-N'-methyl-N-nitrosoguanidine at 30° C. for 20 minutes.

Examples of the vitamine-P compounds are acenocoumarin, apiin, coumetarol, cyclocumarol, dicumarol, diosmetin, esculetin, esculin, ethyl-bis-coumacetate, 3,3'-ethylidene-bis-4-hydroxy-coumarin, heseperetin, hesperidin, morin, naringenin, phenprocoumon quercetin, quercimeritrin, robinin, rutin, scoparone, skimmin, umbelliferone, and warfarin.

A mutant, which is resistant to one of the vitamine-P compounds, is usually resistant to another vitamine-P compounds. The mutant resistant to the vitamine-P compounds is capable of growing on an agar medium which contains the amount of the vitamine-P compound inhibitive to the growth of its parent strain.

The resistance to the vitamine-P compound was determined as follows:

An agar medium of pH 7.0, was prepared by adding the amount of vitamine-P compound shown in Table 1 to a basal medium containing, per deciliter, 3.6 g glucose, 0.1 g $KH_2PO_4$, 0.1 g $MgSO_4.7H_2O$, 1 mg $FeSO_4.7H_2O$, 1 mg $MnSO_4.4H_2O$, 1 g urea, 10.0 μg biotin, 20.0 μg thiamine-HCl and 2 g agar, was put in a glass shallow pan of 10 cm length×5 cm width×3 cm height having glass lid. After having been heated to sterilize, the shallow pan was placed slantwise obtaining a slant medium. On the slant medium the basal medium was poured, and the shallow pan was placed horizontally, and thus concentration gradient plate was prepared.

Each microorganism to be tested, which had previously cultured on a slant of pH 7.0, containing 1 g/dl peptone, 1 g/dl yeast extract and 0.5 g/dl NaCl, for 24 hours, was streaked straight from the higher concentration end of vitamine-P compound of the plate to the lower concentration end. The length of the growth stripe on the plate of the microorganism resistant to the vitamine-P compound in a higher degree is longer than that of the microorganism sensitive to the vitamine-P compound.

The lengths of the growth stripes of the tested microorganisms were measured, and are shown in Table 1.

TABLE 1

| Tested microorganism | | Vitamine-P compound contained in the lower layer of the plate | | Resistance degree (length of stripe (cm)) | |
|---|---|---|---|---|---|
| Mutant | Parent | Compound | Concentration g/dl | Mutant | Parent |
| AJ 11355 | ATCC 14067 | Esculetin | 0.5 | 7.5 | 3.2 |
| AJ 11356 | " | Coumarin | 1.0 | 8.0 | 4.0 |
| AJ 11357 | " | Dicumarol | 1.0 | 6.2 | 3.3 |
| AJ 11360 | ATCC 13869 | Esculetin | 0.5 | 6.6 | 3.3 |

TABLE 1-continued

| Tested microorganism | | Vitamine-P compound contained in the lower layer of the plate | | Resistance degree (length of stripe (cm)) | |
|---|---|---|---|---|---|
| Mutant | Parent | Compound | Concentration g/dl | Mutant | Parent |
| AJ 11361 | " | Coumarin | 1.0 | 7.6 | 4.2 |
| AJ 11362 | " | Dicumarol | 1.0 | 7.0 | 3.6 |
| AJ 11365 | ATCC 13032 | Esculetin | 0.5 | 7.8 | 3.5 |
| AJ 11366 | " | Coumarin | 1.0 | 7.7 | 2.8 |
| AJ 11367 | " | Dicumarol | 1.0 | 7.2 | 4.1 |

The mutants resistant to vitamine-P compound are cultured to produce L-glutamic acid by conventional manner. Namely, the cultivation is carried out under an aerobic condition at a temperature in the range from 30° C. to 40° C.

Even when the mutants of this invention are cultured in a medium containing excessive amount of biotin (5~1000 μg/l) without the addition of surfactant or antibiotic, they produce L-glutamic acid in very high yields.

L-Glutamic acid thus accumulated in the resulted culture liquid can be recovered also by conventional manner.

EXAMPLE 1

An aqueous culture medium was prepared to contain, per deciliter, 10 g (as glucose) cane molasses, 0.1 g $KH_2PO_4$, 0.05 g $MgSO_4.7H_2O$, 0.001 g $FeSO_4.7H_2O$, 0.001 g.$MnSO_4.4H_2O$, 10.0 μg thiamine.HCl, and 1 ml soyprotein acid-hydrolysate, and adjusted to pH 7.0, and 20 ml batches of the culture medium were placed in 500 ml shaking flasks and sterilized.

Each of the medium was inoculated with the respective microorganisms listed in Table 2, and held at 35° C. with shaking during the cultivation, small portions of 40 g/dl urea solution were added to the medium to maintain the pH at from 6.5 to 8.0. After 36 hours of the cultivation, the cultivation was discontinued and the yield(%) based on the sugar used of L-glutamic acid accumulated in the resultant culture liquid was determined.

The results are shown in Table 2.

TABLE 2

| | Yield of L-glutamic acid (%) |
|---|---|
| AJ 11355 | 25 |
| AJ 11356 | 20 |
| AJ 11357 | 32 |
| ATCC 14067 | 5 |
| AJ 11360 | 33 |
| AJ 11361 | 29 |
| AJ 11362 | 31 |
| ATCC 13869 | 6 |
| AJ 11365 | 18 |
| AJ 11366 | 30 |
| AJ 11367 | 30 |
| ATCC 13032 | 5 |

EXAMPLE 2

A culture medium was prepared to contain, per deciliter 3.6 g glucose, 0.2 g urea, 0.1 g $KH_2PO_4$, 0.04 g $MgSO_4.7H_2O$, 0.001 g $FeSO_4.7H_2O$, 0.001 g $MnSO_4.4H_2O$, 1 ml soy protein acid-hydrolysate, 10.0 μg thiamine.HCl, the amount of biotin shown in Table 3, and 20 ml batches of the culture medium were placed in 500 ml shaking flasks and heated to sterilize.

The respective microorganisms listed in Table 3 were inoculated in the culture medium and cultured at 35° C. with shaking. During the cultivation, small portions of 45 g/dl urea solution were added to the culture medium to maintain the pH at from 6.5 to 8.0.

The cultivation was continued to 24 hours, and the yield of L-glutamic acid accumulated in the resulted culture liquid was determined. The results are shown in Table 3.

TABLE 3

| Microorganism | Yield of L-glutamic acid (%) Biotin added (μg/l) | | |
|---|---|---|---|
| | 2 | 20 | 200 |
| AJ 11355 | 46 | 48 | 50 |
| AJ 11356 | 40 | 40 | 51 |
| AJ 11357 | 42 | 41 | 48 |
| ATCC 14067 | 45 | 2 | 0 |
| AJ 11360 | 46 | 47 | 45 |
| AJ 11361 | 49 | 48 | 50 |
| AJ 11362 | 50 | 53 | 48 |
| ATCC 13869 | 43 | 3 | 0 |
| AJ 11365 | 52 | 53 | 49 |
| AJ 11366 | 50 | 53 | 48 |
| AJ 11367 | 52 | 53 | 53 |
| ATCC 13032 | 47 | 4 | 0 |

EXAMPLE 3

An culture medium was prepared to contain, per deciliter, 10 g (as glucose) beet molasses, 0.1 g $KH_2PO_4$, 0.04 g $MgSO_4.7H_2O$, 0.001 g $FeSO_4.7H_2O$, 10.0 μg thiamine.HCl and 0.001 ml anti-forming agent, and 300 ml batches of the culture medium were put in an 1 l-fermenter.

The respective microorganisms listed in Table 4 were cultured aerobically in the medium at 35° C.

Gaseous ammonia was fed into the fermenter so as to maintain the pH at 7.8. After 24 hours of the cultivation, the yields of L-glutamic acid accumulated in the resulted culture liquid were determined, and are shown in Table 4.

TABLE 4

| Microorganism | Yield of L-glutamic acid (%) |
|---|---|
| AJ 11355 | 35 |
| AJ 11361 | 40 |

EXAMPLE 4

A culture medium was prepared to contain, per deciliter, 1 g ammonium acetate, 1 g sodium acetate, 0.1 g $KH_2PO_4$, 0.04 g $MgSO_4.7H_2O$, 0.001 g $FeSO_4.7H_2O$, 0.001 g $MnSO_4.4H_2O$, 0.5 ml soy protein acid-hydrohysate, 20.0 μg thiamine.HCl, 0.1 μg or 10.0 g biotin, and 20 ml batches of the culture medium were placed in 500 ml shaking flasks and heated to sterilize.

The respective microorganisms listed in Table 5 were inoculated in the culture medium, and cultured at 35° C. for 24 hours with shaking.

The yield of L-glutamic accumulated in the resulted culture liquid were determined, and are shown in Table 5.

TABLE 5

| Microorganism | Yield of L-glutamic acid (%) Biotin added to the medium (μg/dl) | |
| --- | --- | --- |
| | 0.1 | 10.0 |
| ATCC 14067 | 46 | 4 |
| AJ 11355 | 45 | 50 |

EXAMPLE 5

A culture medium was prepared to contain, per deciliter, 10 g (as glucose) raw sugar, 0.1 g $KH_2PO_4$, 0.04 g $MgSO_4.7H_2O$, 0.001 g $FeSO_4.7H_2O$, 0.001 g $MnSO_4.4H_2O$, 0.5 g urea, 0.5 ml soy protein acid-hydrolysate, 10 μg thiamine.HCl, and 10 μg biotin, and 20 ml batches of the culture medium were placed in 500 ml shaking flasks. After being sterilized, each batch of the culture medium was inoculated with the respective microorganism listed in Table 6. Cultivation was carried out at 35° C. with shaking. The pH was adjusted during the cultivation with 40 g/dl urea solution to from 6.5 to 8.0.

After 36 hours of the cultivation, the amounts of L-glutamic acid accumulated in the resulted culture liquids were determined. The yields of L-glutamic acid to sugar used are shown in Table 6.

TABLE 6

| Microorganism | Yield of L-glutamic acid (%) |
| --- | --- |
| AJ 11355 | 32 |
| AJ 11356 | 35 |
| AJ 11357 | 41 |
| ATCC 14067 | 5 |
| AJ 11360 | 33 |
| AJ 11361 | 41 |
| AJ 11362 | 40 |
| ATCC 13869 | 6 |
| AJ 11365 | 29 |
| AJ 11366 | 25 |
| AJ 11367 | 30 |
| ATCC 13032 | 5 |

EXAMPLE 6

A culture medium was prepared to contain, per deciliter, 3.6 g (as glucose) cane molasses, 0.1 g $KH_2PO_4$, 0.04 g $MgSO_4.7H_2O$, 0.001 g $FeSO_4.7H_2O$, 0.001 g $MnSO_4.4H_2O$, 10 μg thaimine.HCl, and 0.5 ml soy protein acid-hydrolysate, and 20 ml batches of the culture medium were placed in 500 ml shaking flasks and heated to sterilize.

Each batch of the medium was inoculated with the respective microorganism shown in Table 7, and held at 31.5° C., 35° C. or 37° C. with shaking. During the cultivation, the pH was adjusted to from 6.5 to 8.0 with 40 g/dl urea solution.

After 24 hours of the cultivation, the yields of L-glutamic acid based on the sugar used were determined and are shown in Table 7.

TABLE 7

| Microorganism | Yield of L-glutamic acid Cultivation temp (°C.) | | |
| --- | --- | --- | --- |
| | 31.5 | 35 | 37 |
| AJ 11360 | 28 | 34 | 37 |
| AJ 11366 | 26 | 31 | 34 |

What is claimed as new and intended to be covered by Letters Patent is:

1. A method for producing L-glutamic acid by fermentation which comprises aerobically culturing in an aqueous culture medium a mutant of the genus Brevibacterium or Corynebacterium resistant to a compound having vitamine-P activity, selected from the group consisting of acenocoumarin, apiin, coumetarol, cyclocumarol, dicumarol, diosmetin, esculetin, esculin, ethyl-bis-coumacetate, 3,3'-ethylidene-bis-4-hydroxycoumarin, hesperetin, hesperidin, morin, naringenin, phenprocoumon, quercetin, quercimeritrin, robinin, rutin, scoparone, skimmin, umbelliferone, and warfarin, and recovering the L-glutamic acid accumulated in the resulted culture liquid.

2. The method of claim 1 wherein the compound having vitamine-P activity is esculetin, coumarin or dicumarol.

3. The method of claim 1, wherein the mutant is *Brevibacterium flavum* NRRL B-12128, *Brevibacterium flavum* NRRL B-12129, *Brevibacterium flavum* NRRL B-12130, *Brevibacterium lactofermentum* NRRL B-12133, *Brevibacterium lactofermentum* NRRL B-12134, *Brevibacterium lactofermentum* NRRL B-12135, *Corynebacterium glutamicum* NRRL B-12138, *Corynebacterium glutamicum* NRRL B-12139, or *Corynebacterium glutamicum* NRRL B-12140.

* * * * *